(12) United States Patent
Bischoff

(10) Patent No.: US 6,789,542 B1
(45) Date of Patent: Sep. 14, 2004

(54) DECORATIVE VALVED TRACHEOSTOMY DEVICE

(75) Inventor: Joshua A. Bischoff, Spring Arbor, MI (US)

(73) Assignee: Bischoff Medical Devices, LLC, Spring Arbor, MI (US)

( * ) Notice: Subject to any disclaimer, the term of this patent is extended or adjusted under 35 U.S.C. 154(b) by 35 days.

(21) Appl. No.: 10/080,748

(22) Filed: Feb. 22, 2002

(51) Int. Cl.[7] .......................... A61M 16/00; A62B 9/02; A62B 9/06
(52) U.S. Cl. .......................... 128/207.16; 128/207.14; 128/207.17
(58) Field of Search .................. 128/207.14–207.18

(56) References Cited

U.S. PATENT DOCUMENTS

| | | | | |
|---|---|---|---|---|
| 2,039,142 A | | 4/1936 | Brehm | |
| 2,786,469 A | * | 3/1957 | Cohen .................. | 128/207.16 |
| 3,844,290 A | * | 10/1974 | Birch et al. ............ | 128/207.16 |
| 4,040,428 A | * | 8/1977 | Clifford ................. | 128/207.16 |
| 4,325,366 A | * | 4/1982 | Tabor .................... | 128/207.16 |
| 4,538,607 A | * | 9/1985 | Saul ...................... | 128/207.16 |
| 4,582,058 A | * | 4/1986 | Depel et al. ........... | 128/207.17 |
| 4,759,356 A | * | 7/1988 | Muir ..................... | 128/207.16 |
| 4,809,693 A | * | 3/1989 | Rangoni et al. ....... | 128/207.16 |
| 5,059,208 A | * | 10/1991 | Coe et al. .............. | 623/9 |
| 5,060,645 A | * | 10/1991 | Russell ................. | 128/207.14 |
| 5,606,966 A | * | 3/1997 | Smith .................... | 128/200.26 |
| 5,666,950 A | * | 9/1997 | Smith .................... | 128/207.14 |
| 5,738,095 A | * | 4/1998 | Persson ................. | 128/207.14 |

* cited by examiner

Primary Examiner—Joseph F. Weiss, Jr.
(74) Attorney, Agent, or Firm—Brooks Kushman P.C.

(57) ABSTRACT

A valved tracheotomy tube device usable with conventional tracheostomy tubes wherein the valve housing is of very low profile and covered with an attractive cap so as to appear as a necklace jewelry piece, and preferably, a necklace of attractive jewelry is associated with the tracheostomy tube support so that the entire device is of an attractive, aesthetically acceptable appearance eliminating the medical configuration and appearance of the device.

20 Claims, 3 Drawing Sheets

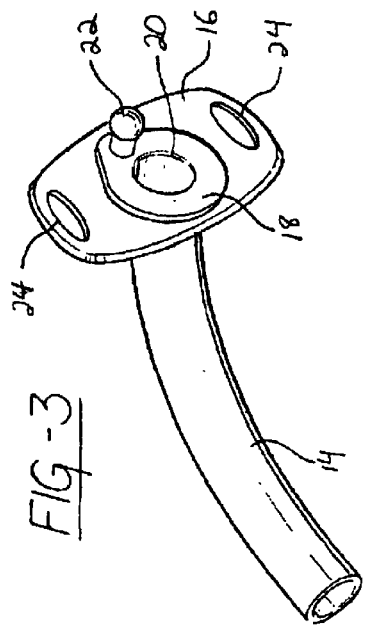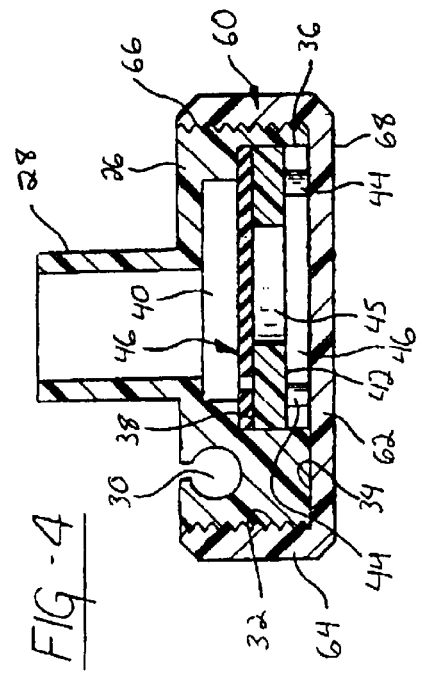

DECORATIVE VALVED TRACHEOSTOMY DEVICE

FIELD OF THE INVENTION

The invention pertains to tracheostomy tubes, and in particular with the improvement of the aesthetics of such tubes and their accessories.

RELATED ART DEVICES

Tracheostomy tubes are inserted in the windpipe of the patient to permit breathing wherein the normal esophagus and windpipe have been damaged or diseased. Tracheostomy tubes are inserted in the neck of the wearer and include an internal portion which extends into the windpipe, and the outer end of the tracheostomy tube is provided with a flange and a support plate located exteriorly of the patient having an opening therein communicating with the tube through which breathing air is inhaled. In many patients, speaking is possible by closing the outer end of the tube after inhalation whereby air may be forced through the vocal cords. The control of air through the tracheostomy tube is often by placing the finger over the opening in the tube support plate during speaking, and releasing the finger valve when inhaling air. Such motions become second nature to the wearer, but are often disconcerting to those the tracheostomy patient is speaking. Tracheostomy patients become objects of curiosity to many, particularly children who do not understand why a person would have a hole in their neck, and tracheostomy patients often become self-conscious of their situation and condition with attendant mental discomfort.

Some tracheostomy tubes have unidirectional valves at their outer ends wherein the valve will permit air to enter the tube, but prevent exhaling through the tube. The use of the one-way valve eliminates the need for the patient to place a finger over the tube opening, but the valve, often of the check valve ball type, requires that the valve structure extend significantly from the tracheostomy tube flange and support plate and significant structure appears at the patient's neck which is, also, of an unusual appearance and the patient is self-conscious of the apparatus. Such speaking valve tracheostomy tubes are offered by Pilling Weck Surgical Company Models 51-8025A and 51-8575, and related model numbers. Accordingly, a tracheostomy tube with a valve has not heretofore been available which is of an attractive appearance and is not a matter of curiosity to the uninitiated.

OBJECT OF THE INVENTION

An object of the invention is to provide a tracheostomy tube apparatus which is capable of being used with conventional tracheostomy tubes wherein a valve may be associated with the tube outer end and the valve structure is of a low profile and appears as an item of attractive neck jewelry which is aesthetically pleasing and unobtrusive.

Another object of the invention is to provide a tracheostomy tube device of the valved type which appears as an item of jewelry, rather than a medical device, and where the device may be easily cleaned and maintained.

Yet another object of the invention is to provide a tracheostomy tube of the valved type having a decorative cap wherein the device will have a jewelry appearance, and by substituting one cap for another, the appearance of the valved device may be readily varied for fashion and color matching purposes.

Another object of the invention is to provide a tracheostomy tube of relatively simple construction wherein a low profile valve housing is associated with the outer end of the tube and the valve housing is located within a decorative cap, while an attractive jewelry-type necklace may be associated with the tube support plate so that the entire device has the appearance of neck jewelry, rather than a medical apparatus.

A further object of the invention is to provide a valved tracheostomy tube apparatus having the appearance of neck jewelry that is readily cleaned, easily maintained by the patient and may be readily varied in appearance in accordance with the costume jewelry aspect of the invention and requires no special skills for the minor modification required to change appearance.

SUMMARY OF THE INVENTION

The valved tracheostomy tube valve of the invention may be employed with a conventional tracheostomy tube having a flange and/or a support plate end to which attachment devices may be affixed, as is commonly known. The valve housing of the apparatus may be attached to many conventional tracheostomy tube support plates and flanges, and may be readily adapted to various attachment devices used by various manufacturers of tracheostomy tubes. In the disclosed embodiment, by way of disclosure, the valve structure is attached to the tracheostomy tube flange by a ball bayonet connection.

The valve housing connected to the tracheostomy tube flange a bayonet connection is preferably formed of an acceptable food grade plastic material and includes a stem extending into the tracheostomy tube constituting an outlet port for the valve housing. Preferably, although not necessarily, the valve housing is of a circular configuration having a decorative cap affixed thereto which maintains the assembly of the valve components, and also provides a decorative aspect to the valve housing making it appear as neck jewelry.

The valve housing includes inlet ports whereby atmospheric air may be drawn into the valve housing. The inlet air is in communication with a relatively flat diaphragm-type valve having a flexible flap and a hinge whereby the edgewise profile of the flap is very small permitting the profile of the valve housing to be of a small size, such as ⅜". Preferably, the length of the valve extending beyond the tube support plate is approximately the dimension of the tube opening. An outlet port or passage is defined in the valve housing communicating with the valve structure and the housing stem and tracheostomy tube whereby air may pass through the valve housing into the tube, but the valve automatically closes and prevents air from flowing from the tube through the valve housing. In this way, a uni-directional air flow from the atmosphere to the tube is provided, eliminating the necessity of the patient to use their finger as a valve.

The valve components, such as the inlet valve plate and diaphragm valve are held in place by a cap threaded upon the exterior of the valve housing. The cap includes a base having a front side which is apparent to the observer, and its front side may be decorated with engravings, semi- or precious stones, or other decorative items. The cap threads upon the valve housing and may be readily attached or removed from the valve housing for decorative changing purposes, or to permit cleaning of the valve housing components.

Preferably, a flexible necklace, such as a gold or silver chain, circumscribes the wearer's neck having ends attached to the tracheostomy tube support plate. The use of the flexible necklace, which is common neck jewelry, further lends to the apparatus a decorative appearance and yet helps maintain the tube in position, and is a substitute for the medical type neck devices commonly used with tracheostomy tubes.

The entire assembly of the low profile valve housing with the decorative cap and the necklace renders a previously objectionable medical device to a type of neck jewelry which is unobtrusive and attractive in appearance, and the invention changes the tracheostomy patient from an object of curiosity to a normal person.

BRIEF DESCRIPTION OF THE DRAWINGS

The aforementioned objects and advantages of the invention will be appreciated from the following description and drawings wherein:

FIG. 1 is a partial front view of a tracheostomy tube patient having a necklace in accord with the invention attached to a tracheostomy tube support plate, and before the valve housing has been attached to the tube flange, FIG. 2 is a view similar to FIG. 1 after the valve housing has been attached to the tube flange and is positioned over the support plate, FIG. 3 is a perspective view of a conventional tracheostomy tube assembly prior to a valve housing being placed thereon, FIG. 4 is a diametrical sectional view of a valve housing in accord with the invention.

DESCRIPTION OF THE PREFERRED EMBODIMENT

Figure 5:
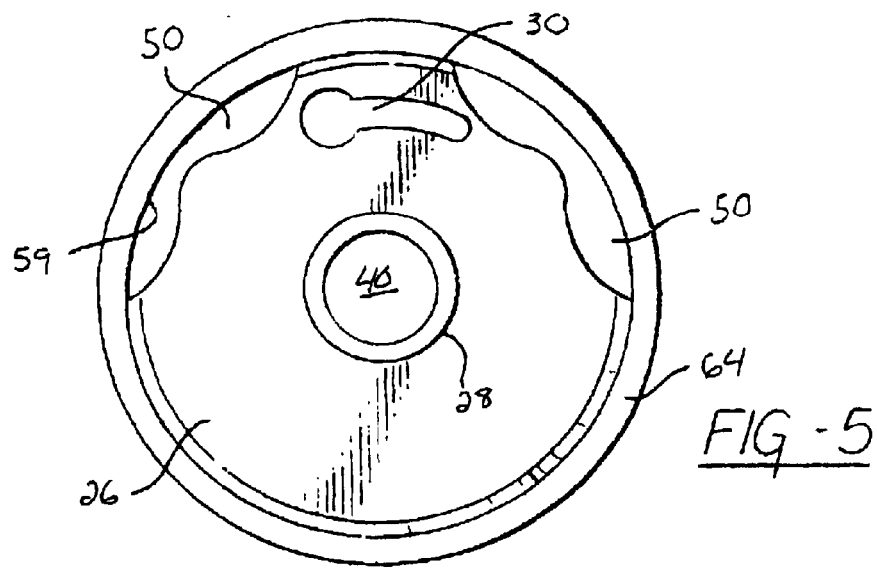
FIG. 5 is a rear view of the valve housing as taken from the top of FIG. 4.
Figure 6:
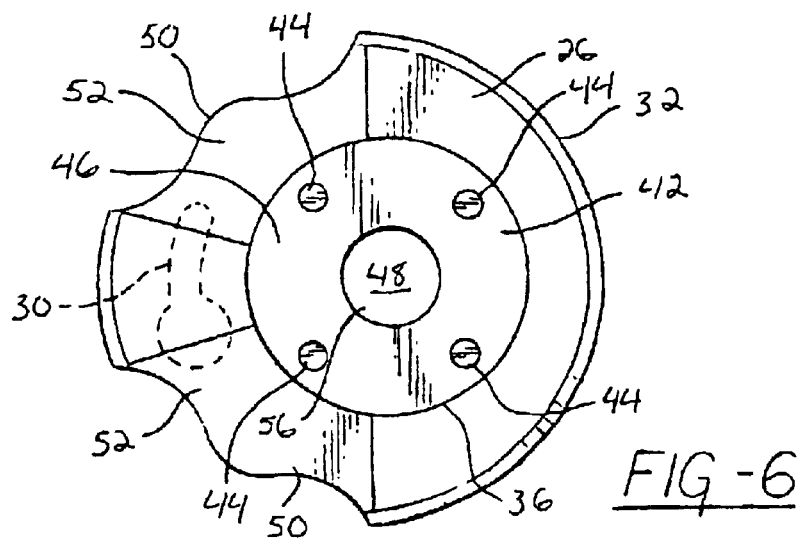
FIG. 6 is a front view of the valve housing upon the removal of the cap illustrating the air inlet ports and the valve cover.

With reference to the drawings, the wearer of the tracheostomy device is shown at 10, and, of course, the wearer includes a neck 12. A typical tracheostomy tube is shown in FIG. 3 wherein the tube 14 will fit into the patient's airpipe and the tube 14 may be located within another tube which has been affixed within the patient. The tube 14 includes an outer end which is flanged at 18 and a support plate 16 is located at the tube outer end below the flange 18. The flange 18 includes the end opening 20 in communication with the tube 14 and a male bayonet ball connection 22 is located upon the flange 18 for attachment of the valve housing thereto, as later described. The bayonet ball 22 includes a short stem supporting a spherical ball for fitting in the female ball bayonet slot in the valve housing, as described below.

The support plate 16 includes ends, and attachment holes 24 are defined adjacent the ends of the support plate 16 for receiving the necklace clasp as later described. The structure shown in FIG. 3 is relatively typical of tracheostomy tube constructions and the invention may be retrofitted to conventional tubes.

The valve housing 26 is preferably formed of a food quality synthetic plastic material, and the valve housing 26 is of a generally circular configuration as will be appreciated from FIGS. 5–8. The valve housing includes a circular central stem 28 which fits within the tracheostomy tube opening 20, and the valve housing 26 includes the female bayonet keyhole slot 30, FIG. 5, for receiving the bayonet ball 22 wherein a slight rotation of the valve housing relative to the flange 18 will connect the valve housing in place upon the flange 18 and the support plate 16.

The generally circular valve housing 26 is provided with an outer periphery upon which threads 32 are defined, and the valve housing includes an outer face 34 which bears against the cap base as later described. Within the outer face 34, a circular opening 36 is defined in the valve housing 26, and as will be appreciated from FIGS. 6–9, the circular opening 36 is off center with respect to the stem 28 and housing 26. The stem 28 is coaxially centered upon the valve housing 26 and is coaxial with the threads 32. The reason the circular open 36 is offset with respect to the stem 28 is to provide clearance for the band keyhole slot 30 and yet a maximum diameter valve may be employed within a relatively confined configuration.

Figure 9:
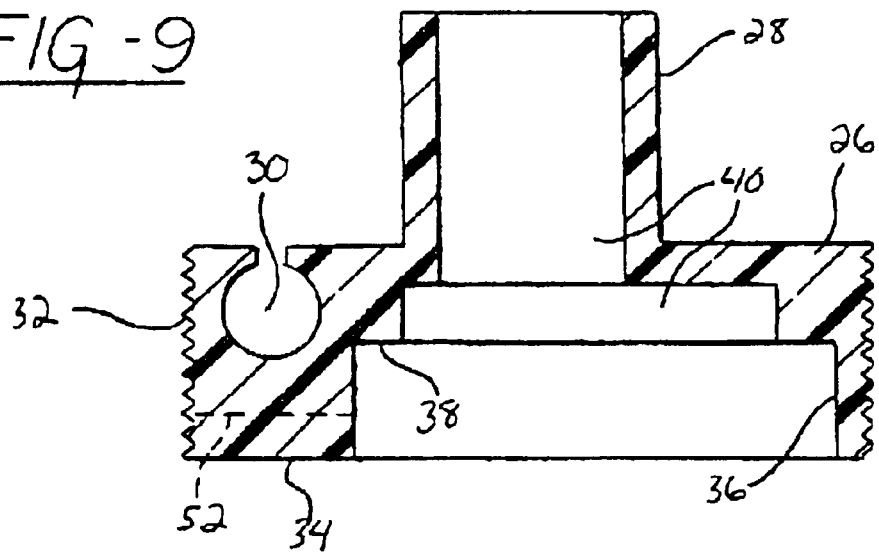
FIG. 9 is an elevational sectional view of the valve housing with the cap and interior components removed.

The circular opening 36 includes a circular shoulder 38 against which the valve engages, as later described, and the outlet port 40 communicates with the interior of the stem 28, FIG. 9, whereby air passing through the valve housing will unidirectionally enter the stem 28 from the valve.

Air into the valve housing 26 is through the washer-like valve cover 42. The valve cover 42 has short posts 44 which space the body of the valve cover from the cap, later described, to provide air passage 46 in the valve cover which is in communication with the central opening 48. The valve cover 42 closely fits within the valve housing circular opening 36, FIGS. 4 and 6.

Air inlet port passages 50 are defined within the valve housing intersecting the rear of the valve housing as will be appreciated from FIG. 5. The inlet ports 50 are defined in the periphery of the valve housing 26, and include radial channels 52 in face 34, FIG. 9, which communicate with the passage 46 of the valve cover 42. In this manner, the inlet air passes into the valve housing through its rear through the inlet ports 50 and into the valve cover 42. Air entering the valve cover flows through the central opening 48 which communicates with the center of the flexible valve 52.

Figure 7:
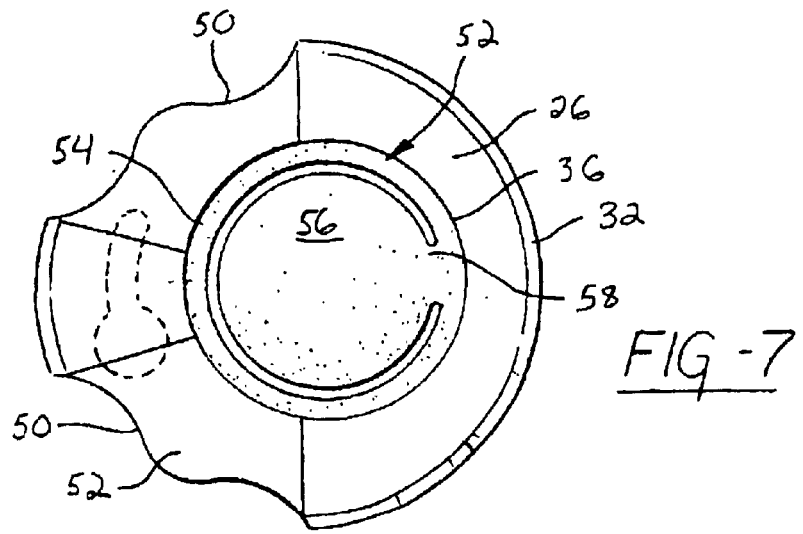
FIG. 7 is a front view of the valve housing upon removal of the valve cover illustrating the flexible valve structure.
Figure 8:
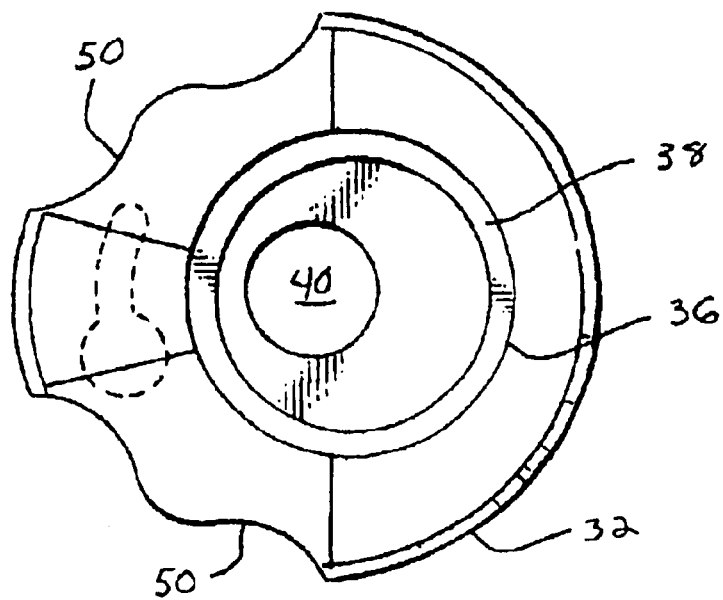
FIG. 8 is a front view of the valve housing upon the removal of the flexible valve.

The valve 52 is best shown in FIG. 7 and is formed of a flexible resilient material such as of rubber, synthetic plastic, or the like which is capable of limited flexing and is resilient enough to return to its original flat configuration when not being deformed by air flowing into the valve housing. The valve 52 includes a peripheral edge portion 54, FIG. 7, which seals against shoulder 38, and a central flat portion 56 is hinged to the edge 54 at 58. As will be appreciated from FIGS. 4 and 7, the flat portion 56 is of a greater diameter than the valve cover central opening 48, and air passing through the opening 48 may pass into the outlet port 40, but the valve flap 56 seals and closes against the smooth back of the valve cover 42 which acts as a valve seat during the exhaling of the wearer 10.

A cap 60 threads upon the valve housing 26. The cap 60 illustrated is plastic, but may be made of metal, or plated plastic or other material. The cap 60 includes a central base 62 and a peripheral axially extending lip 64 having internal threads 66 defined thereon. In this manner, the cap 60 may be easily threaded upon the exterior threads 32 of the valve housing 26. The cap 60 is threaded upon the valve housing 26 until the interior surface of the base 60 engages the front face 34 of the valve housing. Of course, the presence of the inlet ports 50 permit air to enter the rear of the valve housing, pass along the base of the cap in passages 52 and 46 into the valve cover 42.

The cap base 62 includes an exterior front side 68 which is visibly apparent. The front side 68 may include engravings or other decorative features, such as semi-precious or precious stones, or any variety of decorative material. Of course, the cap 60 may be gold or silver plated, or may be of any desired color. For instance, if the cap is formed of a synthetic plastic material, rather than metal, the cap may be colored as desired, and the wearer may have a plurality of caps available so that the cap color matches the clothing being worn.

Normally, with a conventional tracheostomy tube, or even a valved tracheostomy tube, a neckpiece is worn to help maintain the tracheostomy tube in the proper position. The neckpiece is normally of a cloth medical configuration having no aesthetic value or appearance. With the invention, the neck embracing device 70 attached to the support plate 16 is in the form of a decorative flexible necklace or chain 70, such as of gold or silver, and may consist of one or more strands of decorative material, a single strand being shown. The ends of the necklace 70 are attached by clasps 72 to the support plate 16 at openings 24, and by the use of a decorative necklace 70 the entire device obviously is of an attractive jewelry-type appearance and will not attract the curious stares to which tracheostomy patients are so familiar.

As will be appreciated, the valve housing of the invention may be economically produced by injection processes, and the valve housing may be easily cleaned by the wearer merely by removing the cap 60, the valve cover 42 and the valve 52. Upon removal of the components of the valve housing 26 they may be readily cleaned and reinstalled without requiring special skills.

The low profile of the valve housing 26 is important to prevent the device from excessively protruding from the wearer's neck, and by the use of a flat valve 46 a low profile can be maintained. As will be noted from FIGS. 4 and 9, the visible dimension of the assembly extending from the support plate 16 is approximately the diameter of tube opening 20 and stem 28, about 3/8 inches, and this profile and ratio is preferred.

It will be appreciated that with the practice of the invention, a valved tracheostomy tube is rendered aesthetically acceptable, and actually becomes neck jewelry. The psychological benefits of the invention are significant, and it is appreciated that various modifications to the inventive concepts may be apparent to those skilled in the art. For instance, it would be possible to form the configuration of the valve housing to a shape other than circular, and in such instance, the cap may be attached to the valve housing by means other than threads, or the valve could consist of a slightly concave element or be attached to the housing by other than a hinge, and yet the basic inventive concepts be attained, and such modifications are considered to be within the scope of the invention.

What is claimed is:

1. A device mountable on an airway tube, the device comprising:
    a housing mountable on a distal end of an airway tube having a central port in fluid communication with the tube and a distal port for fluid communication with atmospheric air, the distal port having an inlet for receiving the air and an outlet for delivering the air to the central port; and
    a valve supported within the housing and in fluid communication with the ports, the valve movable to an open position during inhalation to permit air to flow from the distal port into the central port to deliver the air to a user's respiratory system, the valve further being movable from the open position to a closed position during exhalation to substantially prevent air flow from exiting the user's respiratory system through the distal port such that a substantial portion of the exhalation air can flow past the user's vocal cords.

2. The device of claim 1, wherein the housing is removably attached to the tube's distal end.

3. The device of claim 1, wherein the housing comprises a threaded periphery, and the device further comprising a decorative cover thread able upon the housing's threaded periphery.

4. The device of claim 1, wherein the housing comprises a lock to lock an outer flange connected to the tube and a decorative flexible necklace attached to the flange and adapted to encircle a user's neck.

5. The device of claim 1, wherein the valve comprises a substantially flat flexible element.

6. The device of claim 5, wherein the valve comprises a substantially flat flexible element hinged to the housing and a valve cover is shaped to surround a periphery of the valve and secure the valve in place by pressure exerted thereto by the cover.

7. The device of claim 5, wherein the housing comprises a central axis at a center point of the central port and a valve axis at a center point of the valve, the valve axis offset from the central axis.

8. A device mountable on an airway tube, the device comprising:
    a cap;
    a housing secured to the cap and mountable on a distal end of the tube, the housing having a central port for fluid communication with the tube and a distal port in fluid communication with atmospheric air, the distal port defined by a channel extending from an inlet to an outlet and covered by the cap such that the covered channel provides a passageway for air received at the inlet to be communicated to the outlet for delivery to the central port; and
    a valve supported within the housing and in fluid communication with the ports, the valve operable during inhalation to permit air to flow from the distal port into the central port to deliver the air to a user's respiratory system, the valve further operable during exhalation to substantially prevent air flow from exiting the user's respiratory system through the distal port such that a substantial portion of the exhalation air can flow past a user's vocal cords.

9. The device of claim 8, wherein the housing comprises a lock for locking an outer flange connected to the tube and at least one necklace end removably attached to the housing.

10. The device of claim 8, wherein the housing comprises a circular threaded periphery, the cover having threads cooperating with the housing periphery threads to secure the housing thereto.

11. The device of claim 8, wherein the valve comprises a seat and a substantially flat valve element cooperative with the seat to close the valve during exhalation for preventing air flow to the distal port.

12. The device of claim 11, wherein the housing comprises a relief for locking to a protrusion on a base connected to the tube, the base having an outer surface and decorations defined on an outer surface of the base.

13. A valve device for use with an airway tube to deliver air to a user's respiratory system during inhalation and to prevent air flow from exiting the tube during exhalation so that the air can flow past a user's vocal cords, the valve comprising:
- a housing having a central port in fluid communication with the tube and a distal port for fluid communication with atmospheric air, the distal port having an inlet for receiving the air and an outlet for delivering the air to the central port;
- a valve supported within the housing and in fluid communication with the ports, the valve having a flap movable to a first position during inhalation to permit fresh air to flow from the distal port into the tube, the flap further movable to a second position during exhalation to block the distal port and thereby prevent air flow from exiting the tube so that the air can flow past the user's vocal cords.

14. The valve device of claim 13, wherein the outlet of the outer port is offset from the central port.

15. The valve device of claim 13, wherein the housing only comprises the valve, the valve cover, and the cap to limit a thickness of the valve device.

16. The valve device of claim 15, wherein the thickness is less than 3/8 inches.

17. The valve device of claim 13, wherein the distal port comprises a channel extending from the inlet to the outlet, and the device further comprising a cap covering the housing such that the cap covers the channel to define a passageway for air received at the inlet to be communicated to the outlet for delivery to the central port.

18. The valve device of claim 17 wherein the distal port's inlet and the central port are on a same side of the housing and are not covered by the cap.

19. The valve device of claim 17 further comprises a valve cover to secure the valve to the housing by compression provided by the cap, the valve having a first side in contact with the housing and a second side in contact with the cap.

20. The valve device of claim 19, wherein the valve cover further comprises a post to offset the valve from the cap such that air can flow from the distal port to the central port during inhalation.

* * * * *